(12) United States Patent
Hakansson (10) Patent No.: US 9,687,350 B2
(45) Date of Patent: Jun. 27, 2017

(54) PROSTHESIS (71) Applicant: TriMed, Inc., Santa Clarita, CA (US)

(72) Inventor: Anders Hakansson, Malmo (SE)

(73) Assignee: TRIMED, INC., Santa Clarita, CA (US)

( * ) Notice: Subject to any disclaimer, the term of this patent is extended or adjusted under 35 U.S.C. 154(b) by 0 days.

(21) Appl. No.: 14/289,165

(22) Filed: May 28, 2014

(65) Prior Publication Data

US 2014/0358244 A1    Dec. 4, 2014

Related U.S. Application Data (60) Provisional application No. 61/828,806, filed on May 30, 2013.

(51) Int. Cl.
*A61F 2/42* (2006.01)
*A61F 2/30* (2006.01)

(52) U.S. Cl.
CPC .. *A61F 2/4261* (2013.01); *A61F 2002/30331* (2013.01); *A61F 2002/30367* (2013.01); *A61F 2002/30426* (2013.01); *A61F 2002/30482* (2013.01); *A61F 2002/30495* (2013.01); *A61F 2002/30578* (2013.01); *A61F 2002/30884* (2013.01); *A61F 2002/4264* (2013.01)

(58) Field of Classification Search
None
See application file for complete search history.

(56) References Cited

U.S. PATENT DOCUMENTS

| 2007/0100463 A1* | 5/2007 | Aram | A61F 2/3868 623/20.29 |
| 2008/0114464 A1* | 5/2008 | Barnett | A61F 2/3868 623/20.33 |
| 2012/0035737 A1* | 2/2012 | Sanford | A61F 2/389 623/20.33 |

* cited by examiner

*Primary Examiner* — Katrina Stransky
*Assistant Examiner* — Daniel Bissing
(74) *Attorney, Agent, or Firm* — Wood, Phillips, Katz, Clark & Mortimer (57) ABSTRACT A prosthesis having: a) a first assembly with a first base portion to be placed against, and operatively secured to, a patient's first bone; and b) a second assembly with a second base portion to be placed against, and operatively secured to, a patient's second bone. The first and second assemblies respectively define first and second surfaces that cooperate with each other to guide articulated movement between the first and second bones. At least one of the first and second base portions is configured to cooperate with a separate first component defining at least a part of one of the first and second surfaces to maintain the first component in an operative state. A second component is configured to define at least a part of the one of the first and second surfaces and can be placed in an operative state selectively in place of the first component.

17 Claims, 8 Drawing Sheets

PROSTHESIS

CROSS-REFERENCE TO RELATED APPLICATIONS

This is a non-provisional patent application claiming priority to U.S. Provisional Ser. No. 61/828,806, filed May 30, 2013, entitled "Wrist Prosthesis", which is hereby incorporated by reference in its entirety.

BACKGROUND OF THE INVENTION

Field of the Invention

This invention relates to prostheses used at locations where adjacent bones articulate and, more particularly, to a prosthesis with cooperating assemblies that can be reconfigured utilizing interchangeable parts.

Background Art

Prostheses are used at many different anatomical locations. Typically, a prosthesis will be made up of separate assemblies secured to adjacent, articulating bones. The separate assemblies have cooperating surfaces that guide relative movement between the bones and are configured to permit, as much as possible, a natural range of motion for a patient's limbs.

Designers of prosthetic devices are driven by a number of different criteria. While comfortable movement in a full range of motion and durability are always overriding objectives in the design process, cost and adaptability of prostheses at each site are also significant considerations. Adaptability relates generally to dimensional variations and material selection, which ideally may be changed during procedures to optimize performance.

It is known to construct the separate assemblies attached to the respective bones from multiple pieces, which allows different materials to be utilized to exploit their particular properties. For example, cooperating assemblies may incorporate one or more components that are non-metal to define surfaces that guide movement between the associated bones. The material defining these surfaces may not have the integrity to facilitate mounting of the prosthesis assemblies to adjacent bones, and thus metal materials are commonly used for this purpose. Joinder of the metal and non-metal components is commonly effected on a permanent basis. As a result, it may be necessary to keep on hand a significant number of prostheses with different configurations to allow them to be selected as a procedure is being performed.

The inventor herein is not aware of any existing prosthesis that allows metal and non-metal parts thereof to be joined releasably in a manner whereby components defining guide surfaces can be readily and practically interchanged to optimize a configuration during the performance of a procedure to implant the prosthesis.

Another limitation associated with these assemblies is the manner in which metal and non-metal parts, or for that matter like composition components, are held together. One common construction utilizes a truncated conical projection on one part of the assembly that fits in a complementary receptacle in another part of the assembly. It is difficult to maintain precise tolerances between the projections and recesses, as a result of which the projections may penetrate the recesses to different depths, whereby the effective overall dimension of the resulting assembly may be only imprecisely predictable. This may result in either tensioned or loose prosthetic connections, which are both detrimental conditions.

The industry continues to seek improved alternative designs that focus on the above design criteria and objectives.

SUMMARY OF THE INVENTION

In one form, the invention is directed to a prosthesis which includes: a first assembly having a first base portion that is configured to be placed against, and operatively secured to, a patient's first bone; and a second assembly having a second base portion that is configured to be placed against, and operatively secured to, a patient's second bone that articulates relative to the first bone. The first and second assemblies respectively define first and second surfaces. The first and second surfaces are configured to cooperate with each other to guide articulated movement between the first and second bones. At least one of the first and second base portions is configured to cooperate with a separate first component which defines at least a part of one of the first and second surfaces to maintain the first component in an operative state as part of its respective first or second assembly. A second component is configured to define at least a part of the one of the first and second surfaces and is configured to be placed in an operative state selectively in place of the first component.

In one form, the one of the first and second assemblies has a first part. There are first and second connectors, respectively on the first part and first component, that are configured to cooperate to releasably maintain the first component in the operative state.

In one form, the one of the first and second assemblies is configured so that the first and second connectors define confronting surfaces that block the first component in the operative state.

In one form, the one of the first and second assemblies is configured so that the first and second connectors are engaged as an incident of the first part and first component being moved relative to each other.

In one form, the one of the first and second assemblies is configured so that the first and second connectors are engaged through snap fitting as an incident of the first part and first component being moved relative to each other.

In one form, the first part and first component are configured so that the first and second connectors are engaged as an incident of the first part and first component being placed in a pre-assembly relationship and thereafter relatively moved around a first axis into an engaged relationship.

In one form, the first and second connectors are configured to define first and second surfaces that: a) face axially oppositely to each other relative to the first axis; and b) are placed in confronting relationship as an incident of the first part and first component changing from the pre-assembly relationship into the engaged relationship.

In one form, the first and second connectors are configured to define third and fourth surfaces that: a) face circumferentially oppositely relative to the first axis; and b) are placed in confronting relationship as an incident of the first part and first component changing from the pre-assembly relationship into the engaged relationship.

In one form, at least one of the first and second connectors has a deflectable element on which one of the third and fourth surfaces is defined. The deflectable element is configured to reposition as the first part and first component are changed from the pre-assembly relationship into the engaged relationship so as to allow the third and fourth surfaces to move past each other and into confronting relationship.

In one form, there are third and fourth connectors, one each on the first part and first connector, which cooperate to maintain the first component in the operative state in conjunction with the first and second connectors.

In one form, the third and fourth connectors are configured to cooperate with each other in substantially the same manner as the first and second connectors cooperate with each other.

In one form, the invention is directed to a combination including the first and second components. The first and second components have either the same configuration or a different configuration.

In one form, the deflectable element is formed as one piece with the first part or first component on which the deflectable element is formed.

In one form, the deflectable element is formed as a separate part on one of the first part and first component.

In one form, the deflectable element is in the form of a split ring.

In one form, the first part and first component are configured so that the first and second connectors are engaged as an incident of the first part and first component being placed in a pre-assembly relationship and thereafter relatively moved along a line into the engaged relationship.

In one form, the first and second assemblies each has a central axis and there is an axially projecting post on one of the first part and first connector and a receptacle into which the axially projecting post extends with the first part and first component in the engaged relationship.

In one form, the axially projecting post has a stepped diameter. The receptacle has a stepped diameter that is complementary to the stepped diameter of the axially projecting post.

In one form, the first part and first component are made from different materials.

In one form, the invention is directed to a method of using the prosthesis described above. The method includes the steps of: providing the prosthesis described above; operatively securing the first base portion to one of a patient's hand and radius; and operatively securing the second base portion to the other of the patient's hand and radius.

DETAILED DESCRIPTION OF THE PREFERRED EMBODIMENT

Figure 1:
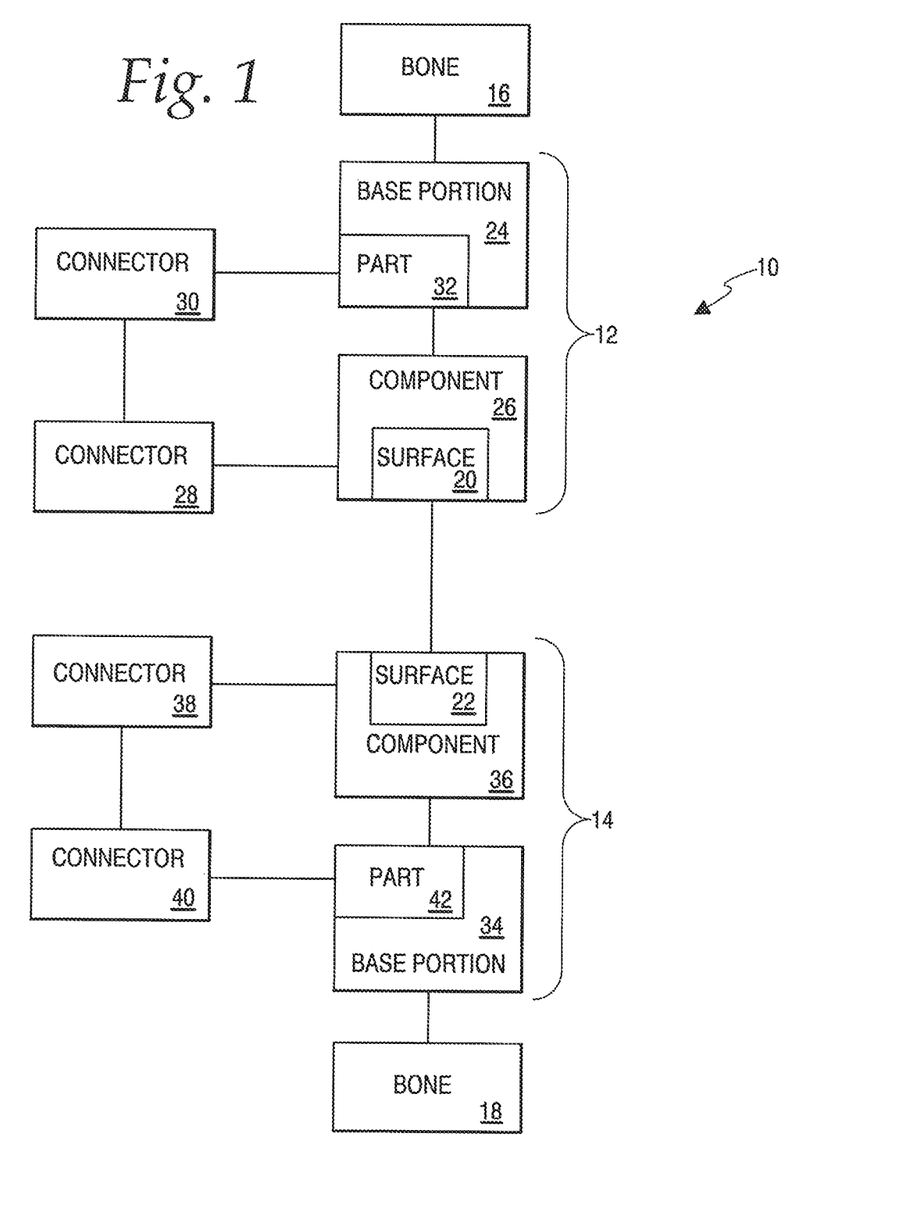
FIG. 1 is a schematic representation of a prosthesis, according to the present invention, including cooperating assemblies that are joined to separate bones that articulate relative to each other.

In FIG. 1, a prosthesis, according to the present invention, is shown in schematic form at 10. The prosthesis 10 consists of separate assemblies 12, 14 which respectively attach to separate bones 16, 18 relative to which there is articulation. Ideally, the use of the prosthesis 10 permits a natural motion, and range of motion, between these bones 16, 18. The assemblies 12, 14 respectively have cooperating surfaces 20, 22 that act against each other to guide movement between the bones 16, 18 in a controlled manner.

The prosthesis 10 is shown in schematic form to encompass a wide variation of components, which include, but are not limited to, those shown in detail in the Figures hereafter described. The schematic showing is intended to encompass those specific components and virtually an unlimited number of variations thereof that would be readily derivable by one skilled in the art with the basic teachings herein in hand.

The assembly 12 has a base portion 24 that is operatively secured to the bone 16 in a manner determined by the particular configuration of the bone 16. The prosthesis 10 may be provided at any location whereat there is articulation between the bone 16 and a separate bone or bones 18.

The assembly 12 has a component 26 that is connected to the base portion 24 through cooperating connectors 28, 30, respectively on the component 26 and a part 32 of the base portion 24.

In this embodiment, the assembly 14 is of the same general construction as the assembly 12, to include a base portion 34, corresponding to the base portion 24, that is operatively secured to the bone 18. The base portion 34 engages a component 36, corresponding to the component 26, upon which the surface 22 is formed. The base portion 34 and component 36 are engaged and maintained together through cooperating connectors 38, 40, with the former being on the component 36 and the latter being on a part 42 of the base portion 34.

One specific, exemplary application of the prosthesis 10 will be described with respect to an individual's wrist, with the bone 16 actually being multiple bones making up a person's hand H (FIG. 13) and the bone 18 making up the person's radius. It should be understood that this particular application is intended only to be an example of a suitable site for the prosthesis 10. The prosthesis 10 is intended for use between any articulating bone pair.

Referring now to FIGS. 2-10, the assembly 14 is shown with the aforementioned base portion 34 and cooperating component 36. The component 36 defines the surface 22. The part 42 of the base portion 34 has connectors 40a, 40b that respectively cooperate with connectors 38a, 38b on the component 36 to maintain the component 36 in an operative state. It is not required that there be multiple paired connectors 38a, 40a; 38b, 40b as depicted, though that is preferred in this particular embodiment.

Figure 2:
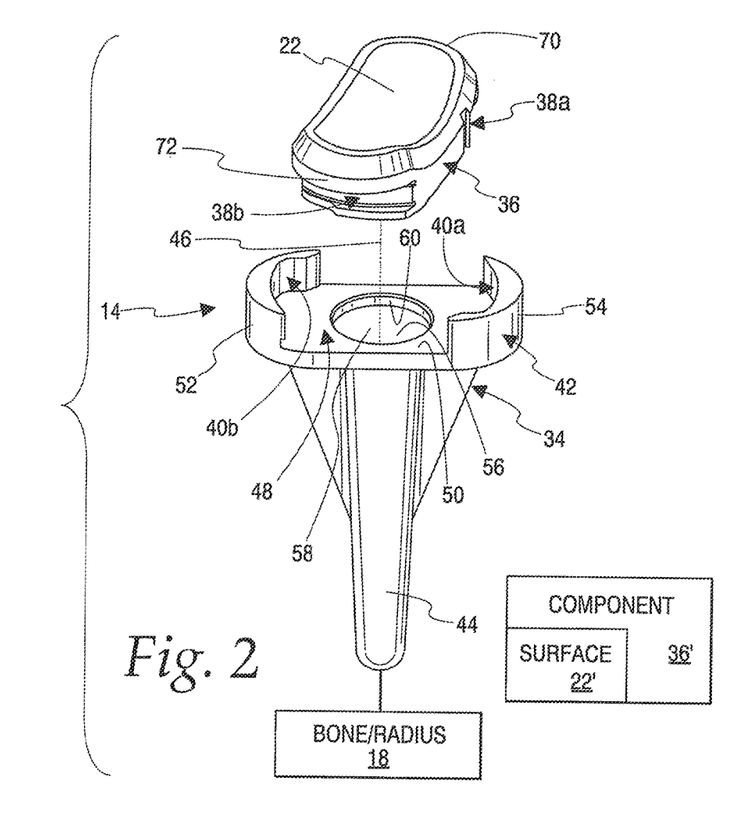
FIG. 2 is an exploded, perspective view of a specific form of one of the assemblies shown in FIG. 1 and including a base portion and a component that is releasably connected to a part of the base portion.

The base portion 34 has an elongate stem 44 having a generally conventional shape for anchoring to a person's radius. This particular configuration should not be viewed as limiting as it is but representative of different base portions that are configured to be placed against and operatively secured to a patient's bone/radius 18.

The assembly 12, as seen in FIGS. 12-20 and 22, has the aforementioned base portion 24 configured to be placed against, and operatively secured to, a patient's bone(s)/hand 16/H that articulates relative to the bone/radius 18. The surface 20 is defined by the component 26 that is attached to the part 32 of the base portion 24. The post 32 defines the connector 30 on the base portion 24 that cooperates with the connector 28 to maintain the component 26 in the operative state therefor as shown clearly in FIG. 16.

While it is preferred that the assemblies 12, 14 have the specific construction described herein, it should be understood that either of the assemblies 12, 14 could cooperate with another assembly having a substantially different configuration.

As explained in greater detail below, the assembly 14 is preferably configured so that the component 36 can be releasably maintained in its operative state in association with the base portion 34. Accordingly, a component shown schematically at 36' in FIG. 2, defining a surface 22', corresponding in function to the surface 22, can be placed in an operative state selectively in place of the component 36. The component 36' may have the same configuration as the component 36, or a different configuration. The different configuration may be to alter the overall dimensions of the assembly 14, change the configuration of the surface 22, 22', change the material of the surface 22, 22' etc. Alternatively, if the components 36, 36' are identical, the interchangeability facilitates replacement as may be necessitated by wear, injury, or some other cause.

Figures 15, 16, 17:
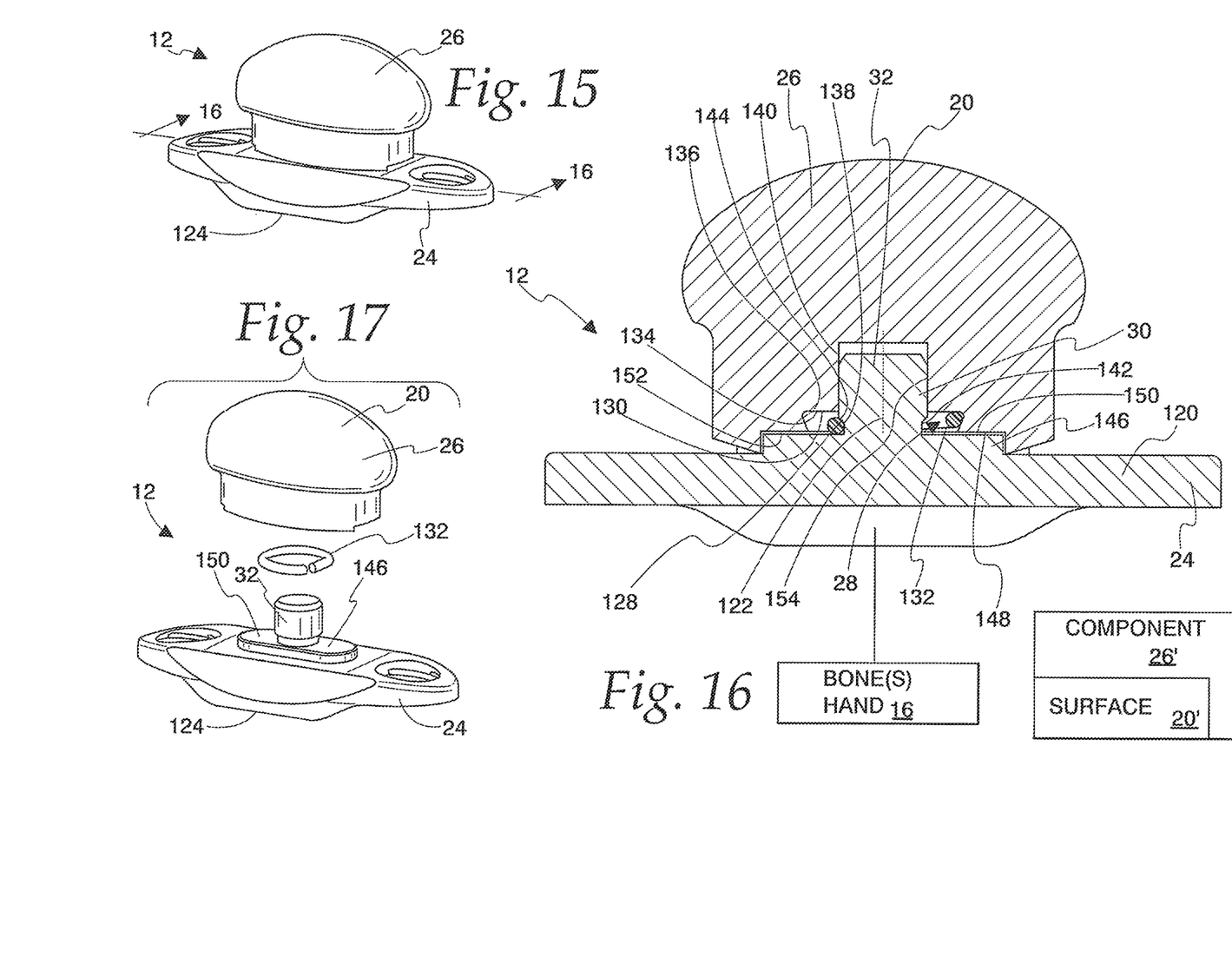
FIG. 15 is a reduced, perspective view of the assembly in FIG. 12 in an assembled state.
FIG. 16 is a cross-sectional view of the assembly taken along line 16-16 of FIG. 15.
FIG. 17 is a reduced, exploded, perspective view of the assembly in FIG. 12 and from a different perspective.

While the assembly 12 could be made to allow separation of the component 26 from the base portion 24, even with a permanent connection, flexibility is afforded by reason of the assembly process as described hereinbelow. As shown in FIG. 16, a separate component 26', with a surface 20', can be used in place of the component 26, as at the time of the surgical implantation of the prosthesis 10. Any number of components may be kept on hand with different configurations having different dimensions, configurations for the surface 20, 20', surface materials, etc.

For both embodiments, the selection of the component 26, 26', 36, 36' may be dictated by a particular material or construction best adapted for the application. In all embodiments, the material making up the components 26, 26', 36, 36' and base portions 24, 34, may be the same or different, as a particular application dictates.

Referring now to the details of the assembly 14 in FIGS. 2-11, in a preferred form, the connectors 38a, 40a, 38b, 40b are configured to be engaged as an incident of the component 36 being moved relative to the part 42 of the base portion 34. More specifically, the part 42 of the base portion 34 has a generally elliptical shape as viewed along a central axis 46 for the assembly 14. The part 42 is axially undercut to define a nominally elliptically-shaped recess at 48 bounded by a generally flat surface 50 and axially projecting arcuate wall portions 52, 54 at the ends along the major axis of the elliptical shape. The surface 50 is undercut to define a cup-shaped receptacle 56 centered on the axis 46. The undercut produces a flat surface portion 58 facing the same direction as the surface 50 and a surrounding annular wall 60 extending fully around the axis 46.

The connectors 38a, 40a and 38b, 40b cooperate with each other in substantially the same fashion. On the arcuate wall portion 52, a rib 62 projects radially inwardly at a location spaced axially from the surface 50. The rib 62 extends less than the full circumferential extent of the wall portion 52.

A radially inwardly facing surface 64 on the wall portion 52, upon which the rib 62 is formed, has a generally arcuate shape opening towards the axis 46. The surface 64 is diverted radially outwardly to define a discrete socket 66. The wall portion 52 terminates at a circumferentially facing surface 68 a short distance from the socket 66.

The component 36 has overall a generally elliptical shape matched to the shape of the recess 48 with a width W and a length L between spaced ends 70, 72 on the major axis of the elliptical shape. The component 36 has an outer perimeter extending around the axis 46. The connector 38b is adjacent the outer perimeter of the component 36.

The end 72 has an arcuate groove 74 to receive the rib 62. The groove 74 produces a "U" shape in cross-section at the end 72, as seen in FIG. 7, with a short leg 76 and long leg 78.

Figures 6, 7, 8, 9, 10:
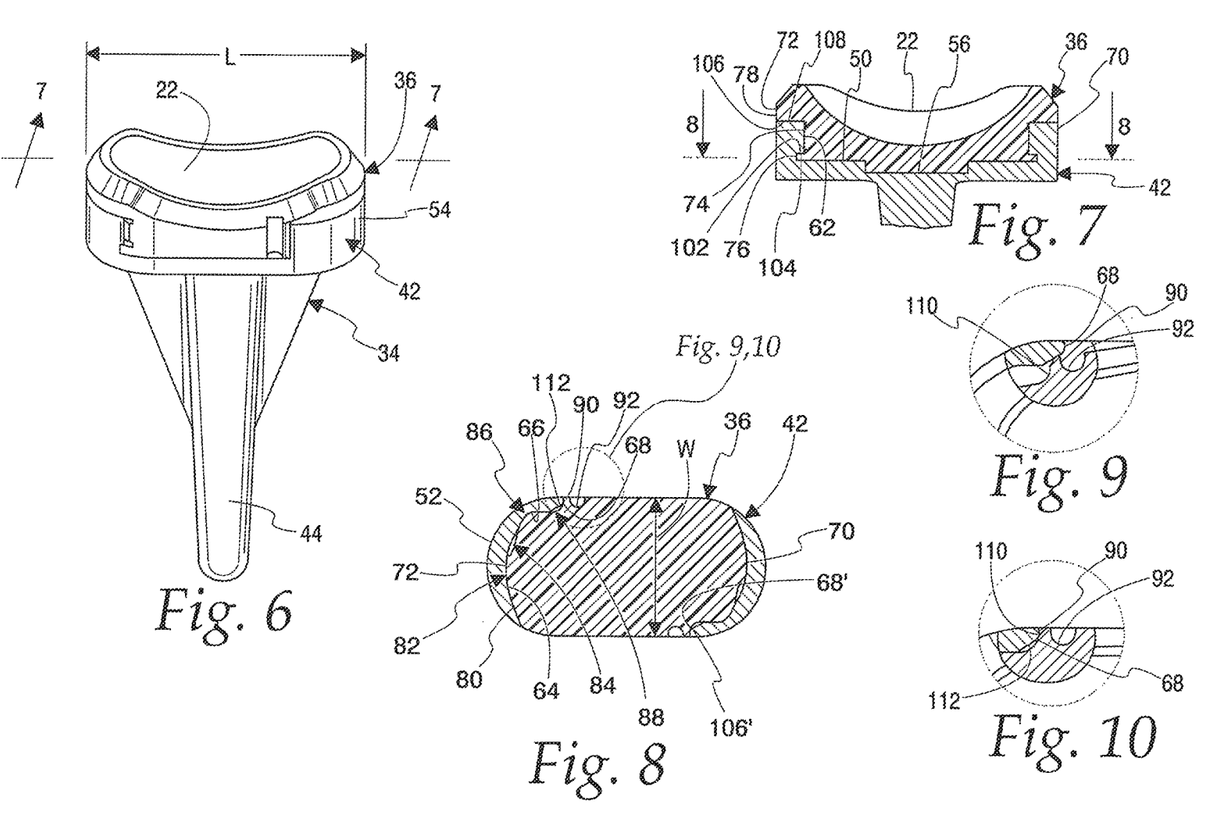
FIG. 6 is a perspective view of the component and part of the base portion in engaged relationship.
FIG. 7 is a cross-sectional view of the assembly taken along line 7-7 of FIG. 6.
FIG. 8 is a cross-sectional view of the assembly taken along line 8-8 of FIG. 7.
FIGS. 9 and 10 are enlarged views of portions of the component and part of the base portion within the circle in FIG. 8 as the component and part of the base portion transition between the pre-assembly and engaged relationships.

The short leg 76, as viewed along the axis 46 in exemplary FIG. 8, has an arcuate free edge 80 with a convex region at 82 that blends successively into a locally concave region at 84, a locally convex region at 86, and a locally concave region at 88, and terminates at a deflectable element 90. A relief 92 is formed adjacent to the deflectable element 90 for reasons hereinafter explained.

A surface 94 on the component 36, facing generally axially oppositely to the surface 22, has a post 96 projecting therefrom. The post 96 has a generally cylindrical shape with an axially facing surface 98.

Figure 3:
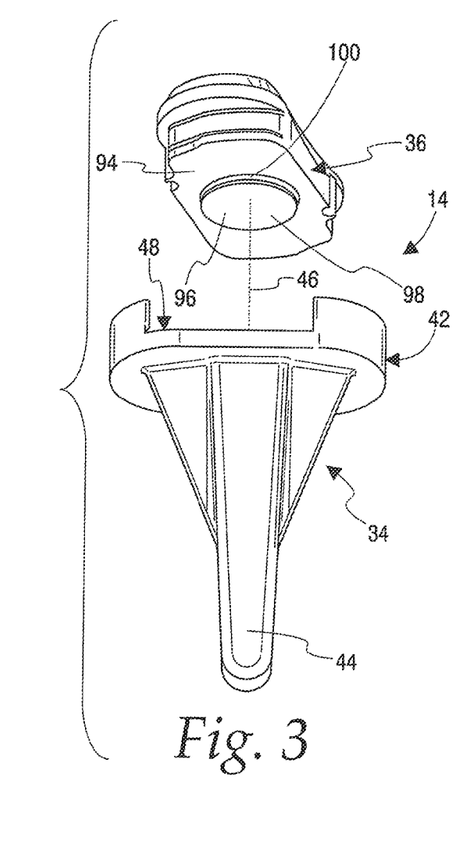
FIG. 3 is a view of the components in the FIG. 2 relationship and from a different perspective.
Figure 4:
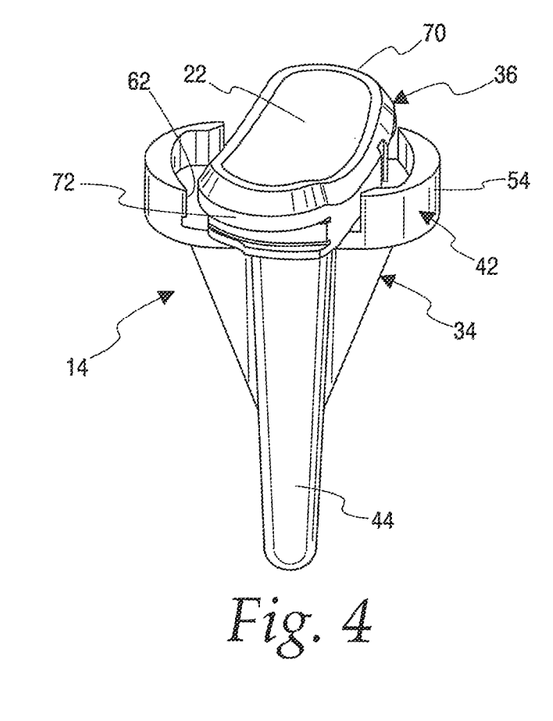
FIG. 4 is a view as in FIG. 2 with the component and part of the base portion in a pre-assembly relationship.
Figure 5:
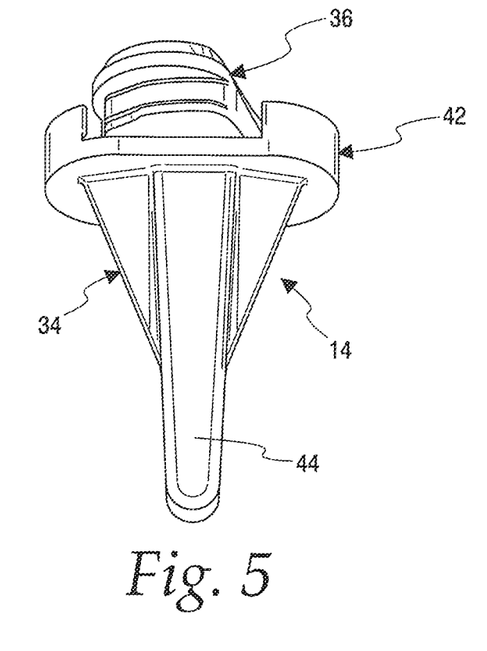
FIG. 5 is a view of the components in the FIG. 4 state and from a perspective corresponding to that in FIG. 3.

To unite the component 36 and the part 42 of the base portion 34, the component 36 is initially situated as shown at FIGS. 2 and 3, spaced axially from the part 42, after which the component 36 and base portion 34 are relatively moved axially in a linear path to against each other into a preassembly relationship with each other and the axis 46, as seen in FIGS. 4 and 5. As this occurs, the surface 98 on the post 96 abuts to the surface portion 58 on the part 42. The post 96 has an outer edge 100 with a diameter that is slightly less than the diameter of the annular wall 60, whereby the post 96 is guided consistently by the wall 60 as the component 36 is turned around the axis 46.

The width W of the component 36 is selected so that the component 36 can be advanced axially from the spaced relationship in FIGS. 2 and 3 to between the wall portions 52, 54 into the pre-assembly relationship with the part 42 of the base portion 34, as shown in FIGS. 4 and 5. In this pre-assembly relationship, with the post 96 seated in the receptacle 56, the surface 94 on the component 36 facially abuts the surface 50 bounding the recess 48.

By then turning the component 36 relative to the part 42 of the base portion 34 around the axis 46, with the pre-assembly relationship of: a) the component 36 and part 42; and b) axis 46 maintained, the rib 62 moves into and along the groove 74. At that point, an axially facing surface 102 on the short leg 76 is placed in confronting relationship with an axially oppositely facing surface 104 on the rib 62. At the same time, an axially facing surface 106 on the long leg 78 abuts to an axially oppositely facing surface 108 on the arcuate wall portion 52. Continued turning of the component 36 causes the short leg 76 to move guidingly along the wall portion 52 until the engaged relationship between the component 36 and part 42 of the base portion 34 is realized, as shown in FIGS. 6-8.

As the engaged relationship is approached, as seen in FIG. 9, the deflectable element 90 is deformed slightly in both circumferential and radial directions, as facilitated to a certain extent by the relief 92. Once the deflectable element 90 clears the circumferentially facing surface 68 on the arcuate wall portion 52, a restoring force in the deformed deflectable element 90 urges a surface 110 thereon, facing circumferentially oppositely to the surface 68, into confronting and abutting relationship. At the same time, the locally convex portion 86 of the short leg 76 aligns with the socket 66 and moves therein. This relationship produces a snap fit connection that can be tactilely sensed as the component 36 and part 42 in the base portion 34 are changed from the pre-assembly relationship into the engaged relationship. Some of the internal forces in the element 90 developed by its deformation may remain with the part 42 and component 36 in engaged relationship to cause the surface 110 to be urged biasably against the surface 68 to firmly maintain the connection.

The region at 112 between the socket 66 and the surface 68 is slightly flattened to facilitate reconfiguration of the deflectable element 90 and movement of the surface 110 thereon up to and past the surface 68. The locally concave region at 84 reduces the binding forces generated between the component 36 and the part 42 of the base portion 34 as the same are changed between the pre-assembly and engaged relationships. This feature is desirable particularly due to the increased friction produced by the locally convex region at 86 that ultimately seats in the socket 66.

To thereafter separate the component 36 from the part 42 of the base portion 34, the component 36 is turned around the axis 46 oppositely to the assembly direction. The confronting circumferentially facing surfaces 68, 106 become wedged against each other, which deforms the deflectable element 90 radially and circumferentially into the relief 92 adequately to allow the deflectable element 90 to turn past the surface 68.

As noted above, the connectors 38a, 40a are configured substantially the same as the connectors 38b, 40b and produce a redundant connection between the component 36 and part 42 of the base portion 34 at a location diametrically opposite to where the connectors 38b, 40b interact. It is conceivable that only one cooperating pair of connectors 38a, 40a; 38b, 40b might be utilized.

With the component 36 and part 42 of the base portion 34 in assembled/engaged relationship, the component 36 is maintained in an operative state by a plurality of confronting surface pairs cooperating between the part 42 of the base portion 34 and component 36—circumferentially facing surface pair 68, 110 and axially facing surface pairs 106, 108; 102, 104; 58, 98; and 50, 94. The short leg 76 becomes captive between the axially oppositely facing surfaces —104 on the rib 62 and 50 bounding the recess 48. The rib 62 becomes captive between the axially oppositely facing surfaces 102, 106 on the component 36. At the same time, the circumferentially facing surfaces 68, 110 interact to block the component 36 and part 42 on the base portion 34 against relative turning around the axis 46.

Similar circumferentially oppositely facing surfaces 68', 106' interact between the connectors 38a, 40a to provide redundant blocking of the component 36 and part 42 of the base portion 34 in assembled relationship. The other facing surface pairs 106, 108; and 102, 104 have counterparts on the connectors 38a, 40a that are not numbered in the drawings.

In this embodiment, the deflectable element 90 is formed as one piece with the component 36. In an alternative form, shown in FIG. 11, a corresponding deflectable element 90' can be provided on a part 42', corresponding to the part 42, that cooperates with a component 36', corresponding to the component 36.

In the depicted embodiment, the component 36 is made from a non-metal material that might be selected from a number of known materials commonly used to form prosthetic guide surfaces. The interacting surfaces, described above, positively support a non-metal component so that it is not prone to significantly changing shape or shifting relative to the part 42 when subjected to anticipated loading forces. The component 36 could be made, in part, or in its entirety, from metal.

Details of the assembly 12 will now be described with respect to FIGS. 12-20 and 22.

Figure 13:
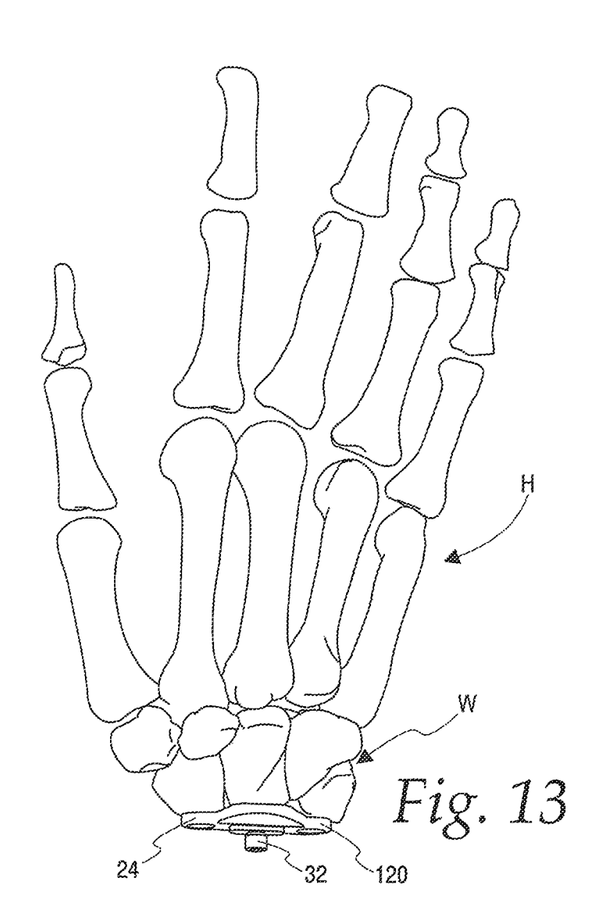
FIG. 13 is a reduced view of the base portion operatively secured to carpal bones in a patient's hand.
Figure 14:
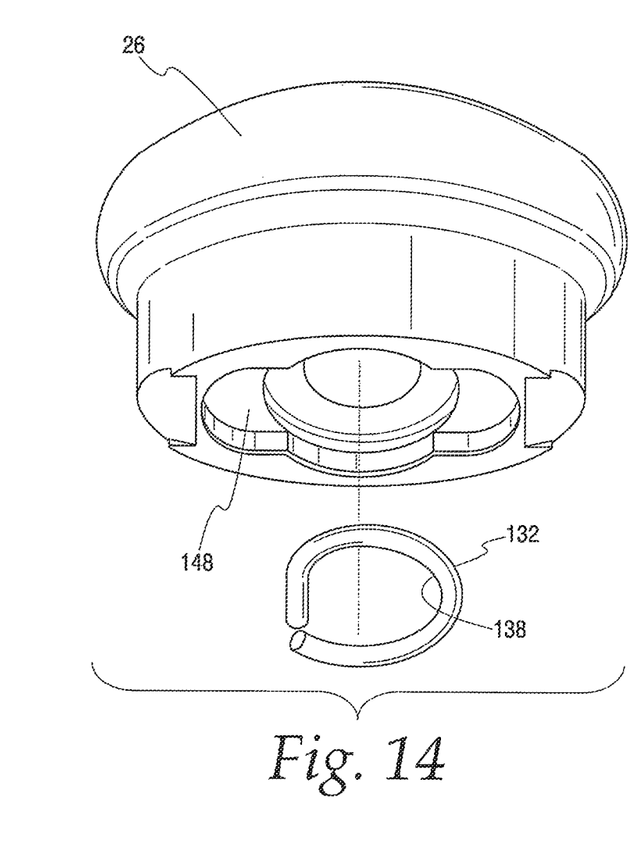
FIG. 14 is an exploded, perspective view of the component in FIGS. 11 and 12 with a split ring that is a part of a connector for joining the component to the base portion.

The base portion 24 has a main wall 120 with an overall generally elliptical shape and a central axis 122. Spaced skirts 124, 126 project away from the main wall 120 at diametrically opposite locations to define an overall "U" shape that is particularly useful to accommodate the carpal bones when the prosthesis is used at the patient's wrist region at W, as shown in FIG. 13. The part 32 consists of a cantilevered post that projects from the main wall 120 axially oppositely to the direction of projection of the skirts 124, 126. The post 32 has a stepped diameter with an undercut to define a generally axially facing annular surface 128 that makes up a part of the connector 30.

The connector 28 is defined by the combination of a stepped receptacle 130 and a split ring 132 placed in one portion 134 thereof. The split ring 132 may take a variety of different shapes. As depicted, the split ring 132 is seated in a radially compressed state in the portion 134 of the receptacle 130 and maintained against axial separation from the receptacle 130 by an angled, annular wall surface 136. The split ring 132, in its seated position as shown in FIGS. 16 and 18, defines an inner edge 138 extending around the axis 122.

Figures 11, 12:
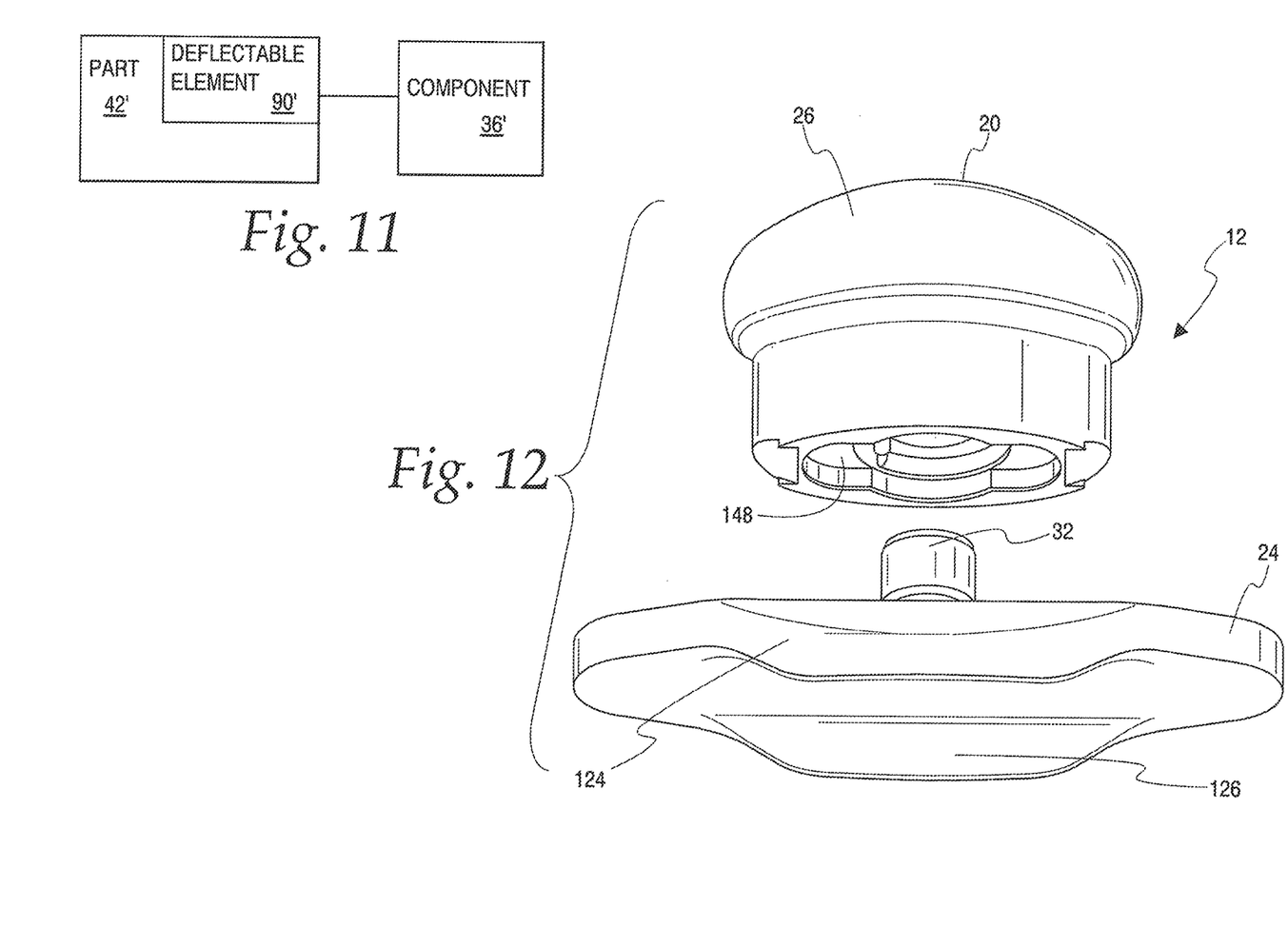
FIG. 11 is a schematic representation of an alternative form of connector cooperating between the component and part of the base portion in FIGS. 2-7.
FIG. 12 is an exploded, perspective view of a component and base portion making up the assembly, as shown in FIG. 1, that cooperates with the assembly shown in FIGS. 2-10.

To place the component 26 in its operative relationship, the component 26 is initially placed in a pre-assembly relationship with the part 32 of the base portion 24, as shown in FIGS. 12 and 17. By then moving the component 26 and part 32 of the base portion 24 axially towards and against each other, the post 32 moves into the opening surrounded by the edge 138 and against a part thereof that radially coincides with its path. A tapered region 140 at the post free end guides the post 32 into this opening, which becomes enlarged through radial wedging of the split ring 132 to allow passage of the post 32 therethrough. Once the undercut 142, at which the surface 128 is formed, aligns axially with the split ring 132, the split ring 132, which is locally deformed radially outwardly by the force of the post 32 acting against the edge 138, is at least partially relaxed. As a result, a portion of the split ring 132 moves to against the surface 128 to place an axially facing surface 144 on the split ring 132 in confronting relationship with the surface 128. Ideally, residual restoring forces in the deformed split ring 132 produce a bias on the portion of the split ring 132 so that it is at all times positively urged against the surface 128.

In this embodiment, the base of the post 32 has an enlarged region 146 with a generally elliptical shape that moves into a complementary portion 148 of the receptacle 130 on the component 26. An axially facing surface 150 on the base region 146 abuts to an axially oppositely facing surface 152 bounding the receptacle portion 148 to consistently axially align the component 26 with the post/part 32 of the base portion 24 with the component 26 in its operative state. The base region 146 and receptacle portion 148 are relatively configured so that a slight turning of the component 26 may occur relative to the part 32 on the base portion 24 around the axis 122 to permit an additional dimension of movement between the bones 16, 18. Alternatively, a tightly keyed connection may be established.

Figures 18, 19, 20:
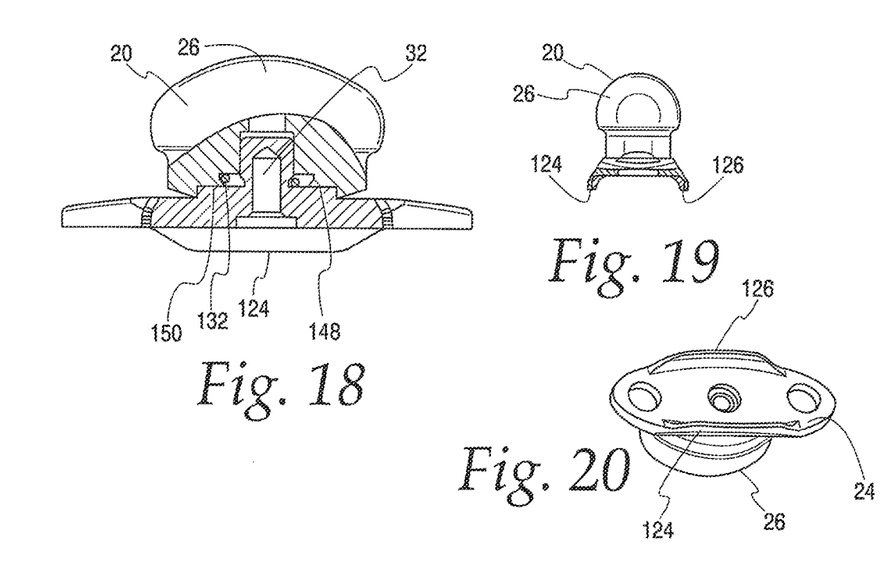
FIG. 18 is a reduced, partial cross-sectional view of the assembly in FIG. 17 with all parts thereof in an assembled state.
FIG. 19 is a reduced, end elevation view of the assembly in FIGS. 12-18.
FIG. 20 is a view of the assembly from a different perspective than in FIG. 19.

By reason of axially moving the component 26 and post/part 32 of the base portion 24 from the pre-assembly relationship in FIGS. 12 and 17 into the engaged relationship as shown in FIGS. 16 and 18, a snap-fit connection is established. Once the split ring 132 is driven into the undercut 142, the user can tactilely sense that the component 26 has realized its operative state and is positively maintained in its operative state. The cooperating surfaces 128, 144 block the component 26 in its operative state.

The split ring 132 functions as a deflectable element that is repositioned as the component 26 and post/part 32 of the base portion 24 are changed from the pre-assembly relationship into the engaged relationship so as to allow the surfaces 128, 144 to move past each other and into confronting relationship.

In this embodiment, the split ring/deflectable element 132 is formed separately from the first part 32. A construction could be devised so that a separate element is not required to perform the function of the split ring.

In the depicted embodiment, the post 32 has a stepped diameter by reason of the undercut 142 and the enlarged base region 146. The receptacle 130 for the post 32 is likewise stepped to receive the post 32 and enlarged base region 146 and provide a space within which the split ring 132 can reside as it is radially enlarged and contracted. The post diameter is slightly less than the diameter of the smaller diameter portion 154 of the receptacle 130. Through this arrangement, the component 26 can be consistently smoothly guided into its operative state.

In the depicted embodiment, the base portion 24 and component 26 are both made from metal, as commonly selected—to maximize structural stability in the case of the base portion 24 and to provide a durable, low friction guide surface 20, in the case of the component 26. Non-metal materials might be used for one, or both, of the base portion 24 and component 26.

Figure 21:
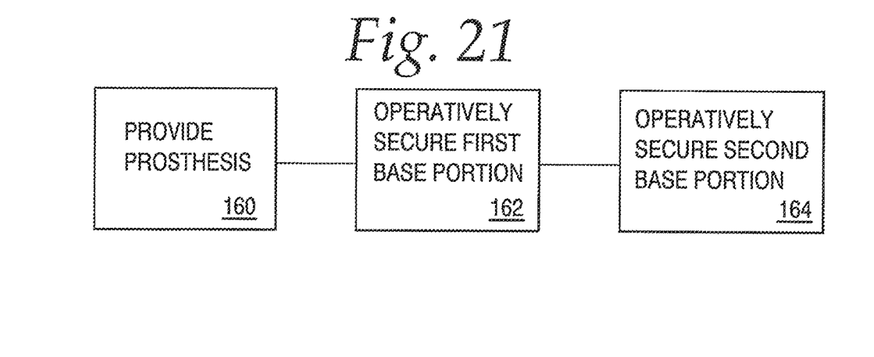
FIG. 21 is a flow diagram representation of a method of using the inventive prosthesis.

With the inventive structure as described above, a method of using a prosthesis can be carried out as shown in flow diagram form in FIG. 21. As shown at block 160, a prosthesis is provided, with first and second base portions, as described above.

As shown at block 162, the first base portion of the prosthesis is operatively secured to one of the patient's hand and radius.

As shown at block 164, the second base portion is operatively secured to the other of the patient's hand and radius.

Figure 22:
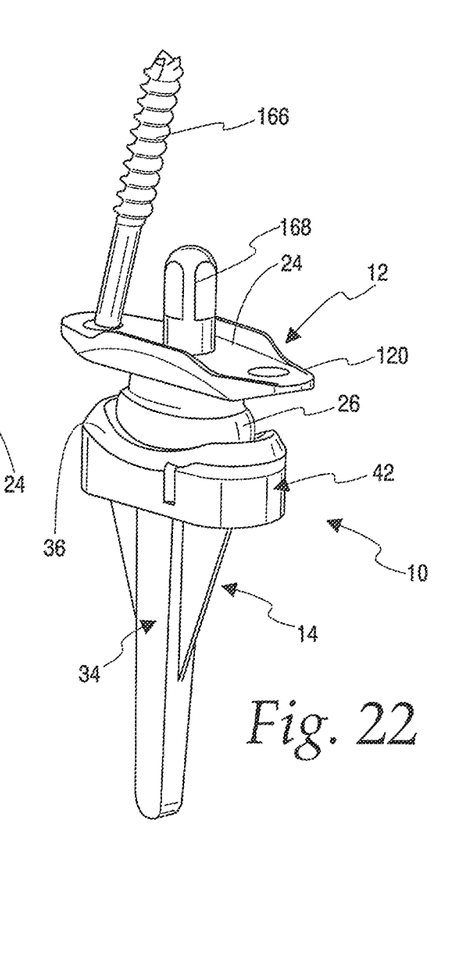
FIG. 22 is a perspective view of the separate assemblies in FIGS. 2-10 and 12-20 in cooperating relationship with each other.

In the event that the base portion 24 is connected to the carpal bones of the hand H, as shown in FIG. 13, fasteners 166, shown in FIG. 22, can be utilized to extend through the base portion 24 into separate carpal bones. A separate post 168 may project from the main wall 120 oppositely to the direction of projection of the post 32. The post 168 can be embedded in a carpal bone for further stabilization of the prosthesis 10. In FIG. 22, the prosthesis 10 is shown in a state wherein the assemblies 12, 14 are operatively engaged.

The foregoing disclosure of specific embodiments is intended to be illustrative of the broad concepts comprehended by the invention.

The invention claimed is:

1. A prosthesis comprising:
a first assembly comprising a first base portion that is configured to be placed against, and operatively secured to, a patient's first bone; and
a second assembly comprising a second base portion that is configured to be placed against, and operatively secured to, a patient's second bone that articulates relative to the first bone,
the first and second assemblies respectively defining first and second surfaces,
the first and second surfaces configured to cooperate with each other to guide articulated movement between the first and second bones with the first and second assemblies operatively secured to their respective bones,
at least one of the first and second base portions configured to cooperate with a separate first component defining at least a part of one of the first and second surfaces to maintain the first component in an operative state as part of its respective first or second assembly,
whereby a second component configured to define at least a part of the one of the first and second surfaces is configured to be placed in an operative state selectively in place of the first component,
wherein the one of the first and second assemblies has a first part and there are first and second connectors, respectively on the first part and first component, that are configured to cooperate to releasably maintain the first component in the operative state,
wherein the one of the first and second assemblies is configured so that the first and second connectors are engaged as an incident of the first part and first component being moved relative to each other around an axis,
wherein the first component has an outer perimeter extending around the axis and the first connector comprises a first axially facing surface adjacent the outer perimeter of the first component,
wherein the second connector comprises a second axially facing surface that confronts the first axially facing surface with the first component in the operative state to thereby prevent the first component from moving axially away from the first part with the first component in the operative state,
the first component and first part configured so that with the first component and first part initially spaced from each other along the axis, the first component and first part can be moved towards each other in near path along the axis into a pre-assembly relationship with the axis and each other, the first component and first part configured so that in the pre-assembly relationship the first component and first part can be engaged as an incident of the first component and first part being moved relative to each other around the axis while maintaining the pre-assembly relationship between: a) the first component and first part; and b) the axis.

2. The prosthesis according to claim 1 wherein the one of the first and second assemblies is configured so that the first and second connectors are engaged through snap fitting as an incident of the first part and first component being moved relative to each other around the axis.

3. The prosthesis according to claim 2 wherein the second axially facing surface and first axially facing surface cooperate to prevent the first component and first part in the engaged relationship from moving away from each other along the axis.

4. The prosthesis according to claim 2 wherein the first and second connectors are configured to define third and fourth surfaces that: a) face circumferentially oppositely relative to the axis; and b) are placed in confronting relationship as an incident of the first part and first component changing from the pre-assembly relationship into the engaged relationship.

5. The prosthesis according to claim 4 wherein at least one of the first and second connectors has a deflectable element on which one of the third and fourth surfaces is defined, the deflectable element configured to reposition as the first part and first component are changed from the pre-assembly relationship into the engaged relationship so as to allow the third and fourth surfaces to move past each other and into confronting relationship.

6. The prosthesis according to claim 1 wherein there are third and fourth connectors, one each on the first part and first connector, which cooperate to maintain the first component in the operative state in conjunction with the first and second connectors.

7. The prosthesis according to claim 6 wherein the third and fourth connectors are configured to cooperate with each other in substantially the same manner as the first and second connectors cooperate with each other.

8. The prosthesis according to claim 1, wherein the first and second components have a different configuration.

9. The prosthesis according to claim 5 wherein the deflectable element is formed as one piece with the first part or first component on which the deflectable element is formed.

10. The prosthesis according to claim 1 wherein there is an axially projecting post on one of the first part and first connector and a receptacle into which the axially projecting post extends with the first part and first component in the engaged relationship, the axis extending through the post with the first part and first component in the engaged relationship.

11. The prosthesis according to claim 10 wherein the axially projecting post has a stepped diameter and the receptacle has a stepped diameter that is complementary to the stepped diameter of the axially projecting post.

12. The prosthesis according to claim 1 wherein the first part and first component are made from different materials.

13. A prosthesis comprising:
a first assembly comprising a first base portion that is configured to be placed against, and operatively secured to, a patient's first bone; and
a second assembly comprising a second base portion that is configured to be placed against, and operatively secured to, a patient's second bone that articulates relative to the first bone,
the first and second assemblies respectively defining first and second surfaces,
the first and second surfaces configured to cooperate with each other to guide articulated movement between the first and second bones,
at least one of the first and second base portions configured to cooperate with a separate first component defining at least a part of one of the first and second surfaces to maintain the first component in an operative state as part of its respective first or second assembly,
whereby a second component configured to define at least a part of the one of the first and second surfaces is configured to be placed in an operative state selectively in place of the first component,
wherein the one of the first and second base portions and first component are configured to be placed in a pre-assembly relationship and thereafter relatively moved about an axis to be placed into an engaged relationship,
wherein there are first and second deflectable elements each on one of: a) the one of the first and second base portions; and b) the first and second deflectable elements deflecting as an incident of the one of the first and second base portions and first component changing from the pre-assembly relationship into the engaged relationship wherein a circumferentially facing surface on each deflectable element confronts a surface on the other of: a) the one of the first and second base portions; and b) the first component,
the deflectable elements each projecting radially relative to the axis from a respective one of: a) the one of the first and second base portions; and b) the first component,
the first and second deflectable elements at diametrically opposite locations.

14. The prosthesis according to claim 1 wherein there is a guide post on one of the first component and base portion on the one of the first and second assemblies that cooperates with the other of the first component and base portion on the one of the first and second assemblies to guide relative movement between the first component and base portion on the one of the first and second assemblies and the first and second axially facing surfaces are spaced radially from the guide post, the axis extending through the guide post with the one of the first and second base portions and first component in the engaged relationship.

15. A prosthesis comprising:
a first assembly comprising a first base portion that is configured to be placed against, and operatively secured to, a patient's first bone; and
a second assembly comprising a second base portion that is configured to be placed against, and operatively secured to, a patient's second bone that articulates relative to the first bone,
the first and second assemblies respectively defining first and second surfaces,
the first and second surfaces configured to cooperate with each other to guide articulated movement between the first and second bones,
at least one of the first and second base portions configured to cooperate with a separate first component defining at least a part of one of the first and second surfaces to maintain the first component in an operative state as part of its respective first or second assembly, whereby a second component configured to define at least a part of the one of the first and second surfaces is configured to be placed in an operative state selectively in place of the first component, wherein the one of the first and second assemblies has a first part and there are first and second connectors, respectively on the first part and first component, that are configured to cooperate to releasably maintain the first component in the operative state, wherein the one of the first and second assemblies is configured so that the first and second connectors are engaged as an incident of the first part and first component being moved relative to each other around an axis, one of the first part and first component having a guide post, through which the axis extends, that guides relative movement between the first part and first component around the axis, wherein the first component has a peripheral edge and the one of the first and second assemblies is configured so that the first and second connectors are engaged through snap fitting as an incident of the first part and first component being moved relative to each other, one of the first and second connectors located at the peripheral edge of the first component.

16. A prosthesis comprising:

a first assembly comprising a first base portion that is configured to be placed against, and operatively secured to, a patient's first bone; and a second assembly comprising a second base portion that is configured to be placed against, and operatively secured to, a patient's second bone that articulates relative to the first bone, the first and second assemblies respectively defining first and second surfaces, the first and second surfaces configured to cooperate with each other to guide articulated movement between the first and second bones with the first and second assemblies operatively secured to their respective bones, at least one of the first and second base portions configured to cooperate with a separate first component defining at least a part of one of the first and second surfaces to maintain the first component in an operative state as part of its respective first or second assembly, wherein the one of the first and second assemblies has a first part and there are first and second connectors, respectively on the first part and first component, that are configured to cooperate to releasably maintain the first component in the operative state, wherein the one of the first and second assemblies is configured so that the first and second connectors are engaged as an incident of the first part and first component being moved relative to each other around an axis, wherein the first component has an outer perimeter extending around the axis and the first connector comprises a first axially facing surface adjacent the outer perimeter of the first component, wherein the second connector comprises a second axially facing surface that confronts the first axially facing surface with the first component in the operative state to thereby prevent the first component from moving axially away from the first part with the first component in the operative state, wherein one of the first part and first component has a guide post, through which the axis extends, that guides relative movement between the first part and first component around the axis.

17. A method of using the prosthesis recited in claim 1, the method comprising the steps of:

providing the prosthesis of claim 1;

operatively securing the first base portion to one of a patient's hand and radius; and operatively securing the second base portion to the other of the patient's hand and radius.

* * * * *

UNITED STATES PATENT AND TRADEMARK OFFICE
CERTIFICATE OF CORRECTION

PATENT NO. : 9,687,350 B2  
APPLICATION NO. : 14/289165  
DATED : June 27, 2017  
INVENTOR(S) : Anders Håkansson Page 1 of 2

It is certified that error appears in the above-identified patent and that said Letters Patent is hereby corrected as shown below:

In the Claims

Claim 1 should read:
1. A prosthesis comprising:
a first assembly comprising a first base portion that is configured to be placed against, and operatively secured to, a patient's first bone; and
a second assembly comprising a second base portion that is configured to be placed against, and operatively secured to, a patient's second bone that articulates relative to the first bone,
the first and second assemblies respectively defining first and second surfaces,
the first and second surfaces configured to cooperate with each other to guide articulated movement between the first and second bones with the first and second assemblies operatively secured to their respective bones,
at least one of the first and second base portions configured to cooperate with a separate first component defining at least a part of one of the first and second surfaces to maintain the first component in an operative state as part of its respective first or second assembly,
whereby a second component configured to define at least a part of the one of the first and second surfaces is configured to be placed in an operative state selectively in place of the first component,
wherein the one of the first and second assemblies has a first part and there are first and second connectors, respectively on the first part and first component, that are configured to cooperate to releasably maintain the first component in the operative state,
wherein the one of the first and second assemblies is configured so that the first and second connectors are engaged as an incident of the first part and first component being moved relative to each other around an axis,
wherein the first component has an outer perimeter extending around the axis and the first connector comprises a first axially facing surface adjacent the outer perimeter of the first component, Signed and Sealed this  
Third Day of October, 2017

Joseph Matal  
*Performing the Functions and Duties of the*  
*Under Secretary of Commerce for Intellectual Property and*  
*Director of the United States Patent and Trademark Office* wherein the second connector comprises a second axially facing surface that confronts the first axially facing surface with the first component in the operative state to thereby prevent the first component from moving axially away from the first part with the first component in the operative state, the first component and first part configured so that with the first component and first part initially spaced from each other along the axis, the first component and first part can be moved towards each other in a linear path along the axis into a pre-assembly relationship with the axis and each other, the first component and first part configured so that in the pre-assembly relationship the first component and first part can be engaged as an incident of the first component and first part being moved relative to each other around the axis while maintaining the pre-assembly relationship between:

a) the first component and first part; and b) the axis.